US008281792B2

(12) United States Patent
Royalty

(10) Patent No.: US 8,281,792 B2
(45) Date of Patent: Oct. 9, 2012

(54) ELECTROMAGNETIC DIAPHRAGM ASSIST DEVICE AND METHOD FOR ASSISTING A DIAPHRAGM FUNCTION

(76) Inventor: John W Royalty, Crystal River, FL (US)

( * ) Notice: Subject to any disclaimer, the term of this patent is extended or adjusted under 35 U.S.C. 154(b) by 1286 days.

(21) Appl. No.: 11/648,908

(22) Filed: Jan. 3, 2007

(65) Prior Publication Data

US 2007/0250162 A1    Oct. 25, 2007

Related U.S. Application Data

(60) Provisional application No. 60/755,413, filed on Dec. 31, 2005, provisional application No. 60/755,414, filed on Dec. 31, 2005, provisional application No. 60/755,415, filed on Dec. 31, 2005, provisional application No. 60/755,416, filed on Dec. 31, 2005, provisional application No. 60/755,424, filed on Dec. 31, 2005.

(51) Int. Cl.
*A61B 19/00*        (2006.01)

(52) U.S. Cl. ....................................................... 128/897

(58) Field of Classification Search ................ 600/9–15; 607/42; 434/265; 128/897–899; 601/41
See application file for complete search history.

(56) References Cited

U.S. PATENT DOCUMENTS

| | | | | |
|---|---|---|---|---|
| 5,128,644 | A | * | 7/1992 | Nellessen ...................... 335/306 |
| 5,498,228 | A | * | 3/1996 | Royalty et al. .................. 600/16 |
| 6,216,030 | B1 | * | 4/2001 | Howard et al. ............... 600/427 |
| 7,006,860 | B2 | * | 2/2006 | Menon ........................... 600/422 |
| 2004/0088015 | A1 | * | 5/2004 | Casavant et al. ................ 607/14 |
| 2005/0085865 | A1 | * | 4/2005 | Tehrani ........................... 607/42 |
| 2006/0122661 | A1 | * | 6/2006 | Mandell .......................... 607/42 |
| 2008/0215106 | A1 | * | 9/2008 | Lee et al. ........................ 607/17 |

FOREIGN PATENT DOCUMENTS

CN        1947676 A   *   4/2007

OTHER PUBLICATIONS

Daniel C. Wiener and Michael T. Jaklitsch, "Surgery of the Diaphragm: A Deductive Approach," Sabiston & Spencer Surgery of the Chest, vol. I, 7th ed., Elsevier Saunders, pp. 510-512.

* cited by examiner

*Primary Examiner* — Charles A Marmor, II
*Assistant Examiner* — Catherine E Burk
(74) *Attorney, Agent, or Firm* — Pillsbury Winthrop Shaw Pittman LLP

(57) ABSTRACT

A diaphragm assist device includes a magnetic mat adapted for mounting inside a human body adjacent the diaphragm. The mat is made from a material responsive to application of an electromagnetic field so as to be movable into compressive relation with the diaphragm in response to application of the electromagnetic field thereto and movable out of the compressive relation to permit the diaphragm to relax when application of the electromagnetic field is discontinued. The device also includes an electromagnetic assembly adapted for surrounding the torso of the human body in functionally cooperative relation with respect to the mat, and for alternately generating and discontinuing the electromagnetic field so that the mat alternately moves into and out of the compressive relation with the diaphragm. The device also includes a controller constructed and arranged to control an intensity level of the electromagnetic field generated by the electromagnetic assembly.

16 Claims, 5 Drawing Sheets

ELECTROMAGNETIC DIAPHRAGM ASSIST DEVICE AND METHOD FOR ASSISTING A DIAPHRAGM FUNCTION

CROSS-REFERENCE TO RELATED APPLICATIONS

This application claims the benefit of priority from U.S. Provisional Patent Application Ser. Nos. 60/755,413, 60/755,414, 60/755,415, 60/755,416, and 60/755,424, all of which were filed Dec. 31, 2005, the contents of which are incorporated herein by reference in their entireties. The present application is related to U.S. patent application Ser. Nos. 11/648,914, 11/648,635, 11/648,636, and 11/648,637, all of which were filed Jan. 3, 2007, and are incorporated herein by reference in their entireties.

BACKGROUND OF THE INVENTION

1. Field of the Invention

The present invention is generally directed to a device and method for assisting a human diaphragm function.

2. Description of Related Art

Elevation of the diaphragm may be caused by various dysfunctions of the diaphragm and may interfere with proper functioning of the lungs and heart. For example, when the diaphragm is abnormally elevated, it may compress the lower lobe of the ipsilateral lung, which may then impair proper functioning of the heart, and may ultimately result in the need for mechanical ventilation, or even death.

Elevation of the diaphragm may be congenital, and may be caused by eventration of the diaphragm or phrenic nerve palsy. Although phrenic nerve pacing is one technique that may used to improve diaphragmatic function, it may be somewhat limited and may not produce normal function an atrophied diaphragm.

Because there is an inherent lack of electrical conductivity in the diaphragm, unlike the heart, placement of multiple surface electrodes on or in the diaphragm typically does not provide uniform contraction of the diaphragm muscle.

The potential exists for a large group of patients with diaphragm dysfunction to benefit once further advances in technology can produce smooth coordinated muscular contraction of the diaphragm.

BRIEF SUMMARY OF THE INVENTION

It is an aspect of the present invention to provide a diaphragmatic assist device to patients suffering from diaphragm dysfunction, as described above.

In an embodiment of the present invention, a diaphragm assist device is provided. The device includes a magnetic mat adapted for mounting inside a human body adjacent the diaphragm. The mat is made from a material responsive to application of an electromagnetic field so as to be movable in a first direction into compressive relation with the diaphragm in response to application of the electromagnetic field thereto and movable in a second direction out of the compressive relation to permit the diaphragm to relax when application of the electromagnetic field is discontinued. The device also includes an electromagnetic assembly adapted for mounting on the human body in functionally cooperative relation with respect to the mat, and for alternately generating and discontinuing the electromagnetic field so that the mat alternately moves into and out of the compressive relation with the diaphragm. The electromagnetic assembly is configured to surround the torso of the human body. The device also includes a sensor for evaluating a force applied to the diaphragm during movement of the mat into compressive relation with the diaphragm and for generating an electrical signal as a function of the force, and a controller constructed and arranged to receive the signal generated by the transducer and for controlling an intensity level of the electromagnetic field generated by the electromagnetic assembly as a function of the signal to thereby control a degree to which the mat compresses the diaphragm.

In an embodiment of the present invention, a method for assisting diaphragm movement within a human body is provided. The method includes generating an electromagnetic field around the body with an electromagnetic assembly, and moving a magnetic mat disposed adjacent the diaphragm in response to application of the electromagnetic field to the mat in a direction away from lungs within the human body.

These and other aspects and advantages of the invention will be apparent from the following description, the accompanying drawings, and the appended claims.

BRIEF DESCRIPTION OF THE DRAWINGS

Embodiments of the invention will now be described, by way of example only, with reference to the accompanying schematic drawings in which corresponding reference symbols indicate corresponding parts, and in which.

DETAILED DESCRIPTION OF THE INVENTION

Figure 1:
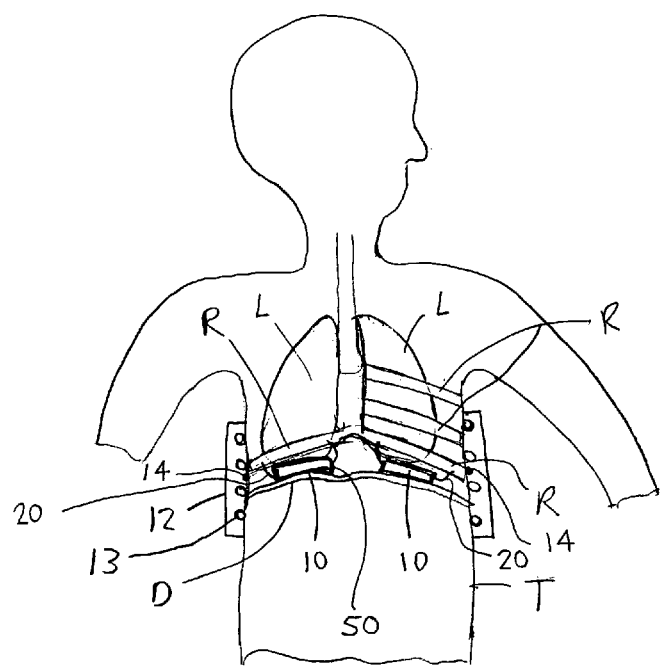
FIG. 1 is a side sectional view of a diaphragm assist device according to an embodiment of the present invention shown inside a human body in a neutral relation with the diaphragm.

FIG. 1 illustrates a diaphragm assist device according to an embodiment of the invention. In the illustrated embodiment, the device includes a magnetic mat 10 which is adapted to be mounted inside the human body, within the thoracic cavity and adjacent the diaphragm D. Preferably, the mat 10 is a permanent magnet made from a flexible ferro-magnetic material, including but not limited to samarium cobalt, neodymium iron, and neodymium iron boron (NeFeBo). It can be appreciated, however, that the mat may comprise other materials (such as a superconductive material) so long as the mat is sufficiently responsive to application of an electromagnetic field to compress the diaphragm in accordance with the principles of the present invention. Regardless of the material used, however, the exterior surface of the mat should be chemically inert, and not immunogenic, so that it does not react with blood, tissue, or organs. If necessary, the mat may be coated or surrounded by an inert substance, including but not limited to polyvinyl chloride (PVC), polytetrafluoroethylene (PTFE), and zinc. In an embodiment, each magnetic mat has a curvilinear, relatively flat shape and is made from neodymium iron boron (NeFeBo) and has a zinc coating.

The mat 10 is supported within the body, preferably in contact with the superior dome of the diaphragm D. If both diaphragms are paralyzed, a magnetic mat may be placed over each diaphragm, as shown in FIG. 1. Preferably, the mat support comprises a plurality of heavy mono-filament threads 20 each having one end secured to the mat and another end secured to the rib cage R (or sternum). The threads are flexible to permit movement of the mat, and should be sufficiently strong to withstand continued flexing without breakage. When the mat is disposed on the diaphragm, the threads 20 may also be sutured through the diaphragm so that the mat will stay in position. It can be appreciated that many alternatives to the mono-filament threads can be used to support the mat, as long as such alternatives maintain the mat in movably supported relation proximate to the diaphragm.

In an embodiment, the mat 10 may also include, a silicone or silicone-like sleeve 50, or, alternatively, each magnetic mat may be covered with silicone or a silicone-like substance to decrease the risk of injury to the diaphragm and also to decrease the risk of contact reactivity. Further details of a suitable sleeve may be found in U.S. patent application Ser. No. 11/648,914, which is incorporated herein by reference. The silicone sleeves that cover each mat may be secured loosely to the patient's ribs and located closely to diaphragmatic tissue. The mat 10 may be placed via thoracoscopy in sections with tongue and groove interlocking joints or hinges. Further details of a magnetic mat that includes sections and hinges may be found in U.S. patent application Ser. No. 11/648,635, which is incorporated herein by reference. The heavy mono-filament threads 20 each have one end thereof secured to the peripheral edges of two opposite sides of the mat, which preferably has a substantially rectangular or oval shape. An incision may be made immediately below the breastbone using the sub-xiphoid approach, and the threads may then be sutured to the rib cage and/or sternum by use of curved trochar sheath. Enough slack should be left in the mono-filament sutures to permit movement of the mat 10 into compressive relation with the diaphragm upon application of an electromagnetic field to the mat 10, as described in further detail below.

Figure 2:
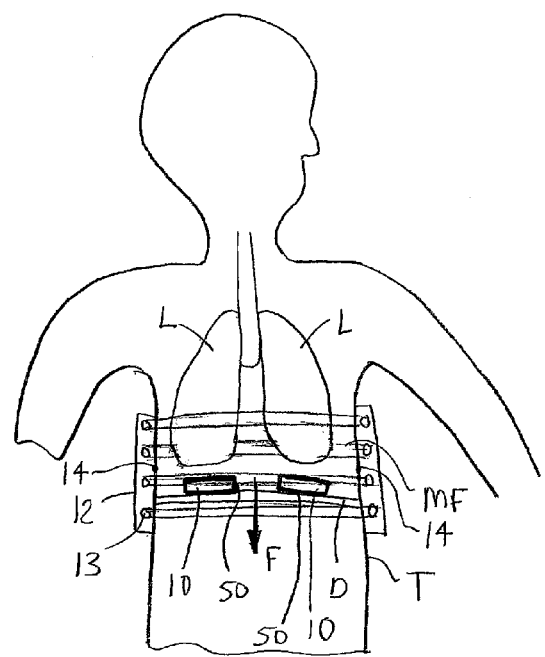
FIG. 2 is a side sectional view of the diaphragm assist device of FIG. 1 shown inside the human body in a compressive relation with the diaphragm.

An electromagnetic assembly 12 is adapted to be mounted externally to the human body, preferably so that it surrounds the torso T of the body, in functionally cooperative relation with respect to the mat 10. The electromagnetic assembly 12 includes at least one induction coil 13 that surrounds the torso of the body and to which a current is provided (preferably by a D.C. battery, not shown) to generate or produce an electromagnetic field MF, which moves the mat in a first direction into compressive relation with the diaphragm and away from the lungs L, as shown in FIG. 2 by arrow F. The operation of the electromagnetic assembly and the magnetic mat may be similar to the electromagnetic assembly and mat disclosed by U.S. Pat. No. 5,498,228, which is incorporated herein by reference in its entirety.

More particularly, the electromagnetic assembly 12 may alternately generate and discontinue the electromagnetic field to alternately move the diaphragm and then permit the diaphragm to relax, thereby assisting the mechanical pumping function of the diaphragm. The magnitude of the force produced will be proportionally dependent on the mat's magnetic field strength, the amount of current traveling through the electromagnetic assembly 12, and the number of current-turns in the electromagnetic assembly 12, but inversely proportional to the distance between the electromagnetic assembly and the mat. Optimal coil function may be seen when the coil is adjacent to the torso, with the shortest distance between the ribs and coil. The current in the coil is controlled in time regarding onset and duration, in power regarding quantity of current delivered, and direction as to reverse polarity.

Figure 3:
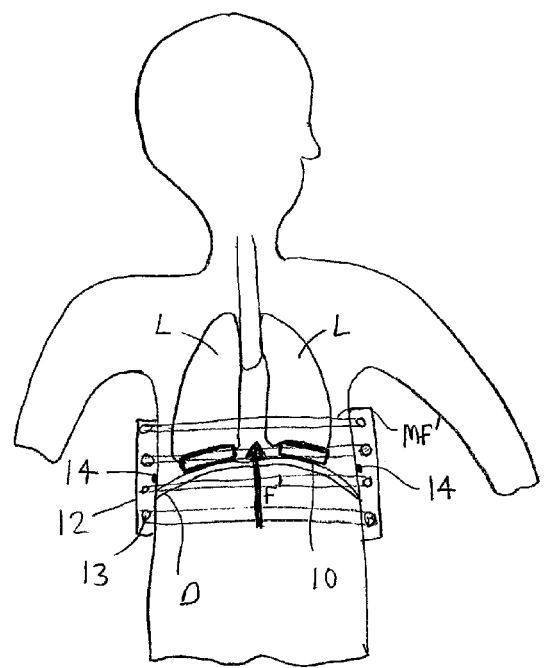
FIG. 3 is a side sectional view of the diaphragm assist device of FIG. 1 shown inside the human body in an expansive relation with the diaphragm.

For example, the electromagnetic assembly 12 may be configured so that the current that is provided to the coil 13 may be reversed so that a second electromagnetic field MF' may be applied to the magnetic mat, which causes the magnetic mat to be moved in a second direction that is away from the diaphragm and toward the lungs L, as shown in FIG. 3 and represented by arrow F'. Because the mat will tend to stick to the diaphragm, the diaphragm will move with the mat 10 via suction. In an embodiment, the mat 10 may be physically attached to the diaphragm D with sutures. When properly timed, such an application and reversal of the electromagnetic field MF may further improve the assistance being provided to the patient, as described in further detail below.

Figure 4:
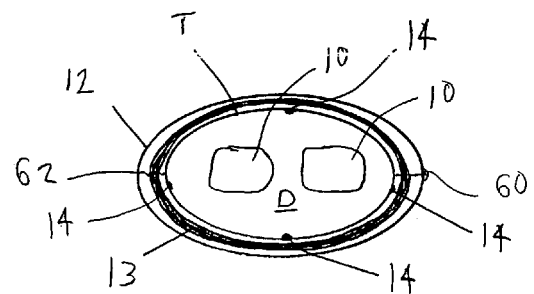
FIG. 4 is a top sectional view of the diaphragm assist device of FIG. 1 with an electromagnetic assembly of the assist device in a closed and locked position.
Figure 5:
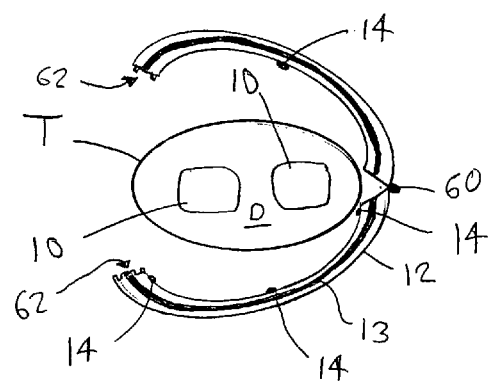
FIG. 5 is a top sectional view of the diaphragm assist device of FIG. 4 with the electromagnetic assembly in an open position.

As shown in FIGS. 4 and 5, the electromagnetic assembly 12 may include a hinge 60 that is configured to allow the electromagnetic assembly 12 to open up like a clamshell. After opening the electromagnetic assembly 12, the patient would lie in the assembly 12 and the assembly 12 may close and lock with a locking structure 62 so that the coil 13 is a continuous structure wrapped around the torso T.

Figure 6:
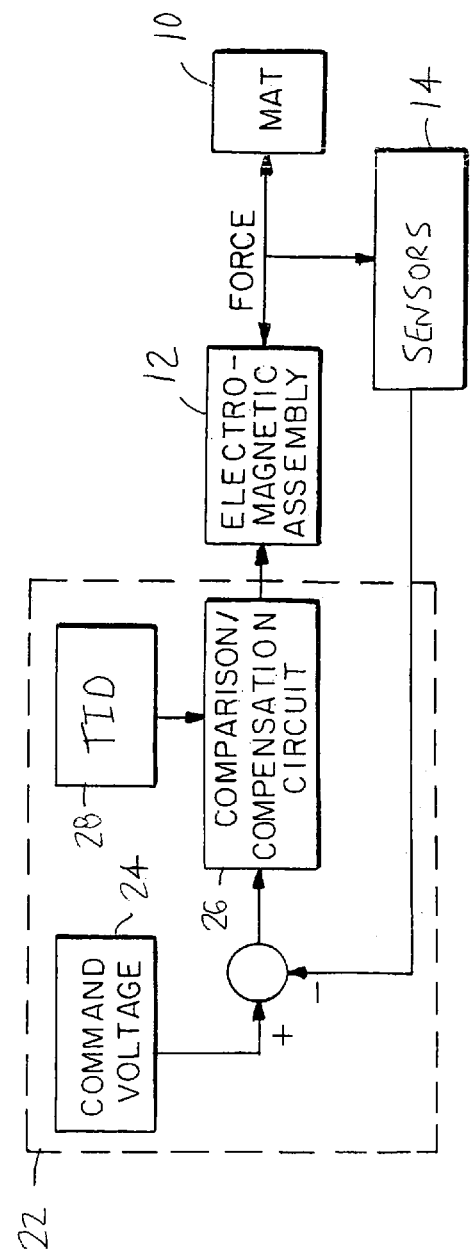
FIG. 6 is a block diagram schematically showing the interrelation of various components of the diaphragm assist device of FIG. 1.

As shown in FIG. 6, the diaphragm assist device also includes a transthoracic impedance device ("TID") 28 that measures transthoracic impedance as the patients breathes. A controller 22 may be programmed with what would be normal transthoracic impedance measurements during inspiration and expiration. As the patient produces, what would be for the patient a normal inspiration, the transthoracic impedance changes, thereby yielding a curve. When inspiration is detected by the device per the curve, current is provided to the coil 13, which moves the magnetic mat 10 through the coil 13 in a direction as determined by the polarity of the mat and the coil, which is set during manufacture.

As the transthoracic impedance device 28 detects expiration, the current provided to the coil 13 may be turned off, or if desired, the current flow may be reversed to that the polarity of the electromagnetic field that is generated by the coil 13 may be reversed to produce opposite movement of the mat 10 and diaphragm. In this manner, both expiration and inspiration may be augmented.

The interaction of the coil 13 with the magnetic mat 10 on the diaphragm D will produce a physical force vector both on the diaphragm D and on the coil 13. Piezoelectric sensors 14 on the electromagnetic assembly 12 may be used to indicate how much force is being applied to the diaphragm D in each direction. This is a feedback mechanism that may be used to avoid excessive force on the diaphragm and potential injury to the diaphragm.

As shown in FIG. 6, the sensors 14 forms part of an electronic feedback/control loop, and function to evaluate the compressive resistance of the diaphragm during movement of the mat into compressive relation with the diaphragm. The transducer 14 senses the compressive pressure or force applied thereto and outputs a voltage proportional to such force or pressure. The controller 22 receives the signal generated by the transducer and controls the intensity of said electromagnetic field generated by the electromagnetic assembly as a function of that signal. As a result, the controller effectively controls the degree to which the mat moves the diaphragm.

More specifically, the controller 22 includes a compensation/comparison circuit 26 (or "compensation circuit") which compares the voltage generated by the sensors 14 to a command voltage generated by command voltage generator 24.

The command voltage corresponds to a predetermined voltage which represents the ideal amount of force required to move the diaphragm. The compensation/comparison circuit 26 measures the difference between the voltage generated by the sensors 14 and the command voltage, and then digitally compensates for such difference so that an appropriate amount of current is sent through the coil 13 in the electromagnetic assembly 12. For example, if the voltage generated by sensors 14 is less than the command voltage, the compensation circuit 26 will ramp up the current sent through the coil 13 and thereby increase the intensity of the magnetic field applied by electromagnetic assembly 12. In contrast, if the voltage generated by sensors 14 is less more than the command voltage, the compensation circuit will decrease the amount of current through the coil 13 and thereby decrease the intensity of the magnetic field applied by the electromagnetic assembly 12. Thus, the intensity or magnitude of the electromagnetic field generated by the electromagnetic assembly is controlled so that the force applied by the mat 10 to the diaphragm remains within a predetermined range with each compressive stroke.

The predetermined amount of force to be applied to the diaphragm in order to obtain the desired output is determined experimentally during an initial procedure wherein a catheter, may placed in the body to monitor pressures in the body near the diaphragm. The pressures are correlated with the voltages generated by the sensors 14, and after several days of experimentation, the catheter may be removed. The sensors 14 thereafter may generate a voltage as a function of the resistance of the diaphragm.

While the magnitude of the electromagnetic field generated by the electromagnetic assembly 12 is controlled by the controller 22, together with the sensors 14, it can be appreciated that the frequency of the electromagnetic field will coincide with the natural contractions of the diaphragm.

The initial treatment course, which may include a series of treatments may be evaluated regarding the current delivered to the coil and pressure production on the diaphragm. The patient's resting title volumes, heart rate, oxygen saturation, and respiratory rate may be monitored to determine treatment efficacy. After the initial series, a treatment program may be set up with given currents. Initial treatments may be performed by a fixed device in which the patient may come to a hospital or doctor's office for initial treatment, and evaluation of the treatment, until a safety protocol has been outlined for that specific patient. Once the patient has safely undergone a series of treatments and current delivery parameters have been established, a portable device may be substituted for home use.

It will be appreciated that the aspects of this invention have been fully and effectively accomplished. It will be realized, however, that the foregoing preferred specific embodiments have been shown and described for the purpose of this invention and is subject to change without departure from such principles. Therefore, this invention includes all modifications encompassed within a spirit and scope of the following claims.

What is claimed is:

1. A diaphragm assist device comprising:
a magnetic mat adapted for mounting inside a human body adjacent the diaphragm, said mat being made from a material responsive to application of an electromagnetic field so as to be movable in a first direction into compressive relation with the diaphragm in response to application of the electromagnetic field thereto and movable in a second direction out of said compressive relation to permit the diaphragm to relax when application of said electromagnetic field is discontinued;
a detector for detecting expiration and/or inspiration in the human body;
an electromagnetic assembly comprising an inductive coil adapted for surrounding a torso of the human body in functionally cooperative relation with respect to said mat, and for alternately generating and discontinuing said electromagnetic field in response to the detection of expiration and/or inspiration by the detector so that said mat alternately moves into and out of said compressive relation with the diaphragm;
a sensor for evaluating a force applied to the diaphragm during movement of said mat into compressive relation with the diaphragm and for generating an electrical signal as a function of said force; and
a controller constructed and arranged to receive said signal generated by said sensor and to control an intensity level of the electromagnetic field generated by said electromagnetic assembly as a function of said signal to thereby control a degree to which said mat compresses the diaphragm.

2. The diaphragm assist device according to claim 1, further comprising a flexible support adapted to secure the mat to a human rib cage.

3. The diaphragm assist device according to claim 2, wherein said flexible support comprises heavy mono-filament threads, and wherein said mat is adapted to be adjacent to a dome of the diaphragm.

4. The diaphragm assist device according to claim 3, wherein said mat is adapted to be located in the thoracic cavity of the human body.

5. The diaphragm assist device according to claim 1, wherein said magnetic mat comprises a permanent magnet surrounded by an insulative layer.

6. The diaphragm assist device according to claim 5, wherein said permanent magnet comprises neodymium iron boron.

7. The diaphragm assist device according to claim 5, wherein said insulative layer comprises zinc.

8. The diaphragm assist device according to claim 1, wherein said controller controls an amount of current which travels through said coil, the amount of current that travels through said coil being proportional to an intensity level of the electromagnetic field generated by said electromagnetic assembly.

9. The diaphragm assist device according to claim 8, wherein said coil comprises a hinge constructed and arranged to allow the coil to be moved between an open position and a closed position.

10. The diaphragm assist device according to claim 9, wherein said coil further comprises a locking structure constructed and arranged to lock the coil in the closed position.

11. The diaphragm assist device according to claim 8, wherein said sensor is a piezoelectric sensor.

12. The diaphragm assist device according to claim 11, said signal generated by said sensor is a voltage proportional to the force applied by the electromagnetic field to the magnetic mat, and wherein the controller comprises a compensation circuit for comparing a command voltage to said proportional voltage and for adjusting the amount of current which travels through said coils as a function of a difference between said command and proportional voltages.

13. The diaphragm assist device according to claim 1, wherein said electromagnetic assembly is constructed and arranged to reverse said electromagnetic field after said electromagnetic field has been discontinued, and wherein said magnetic mat is responsive to application of the reversed electromagnetic field so as to be movable in the second direction.

14. A method for assisting diaphragm movement within a human body, the method comprising:
   detecting expiration and/or inspiration in the human body;
   generating an electromagnetic field around the body with an electromagnetic assembly in response to the detection of expiration and/or inspiration; and
   moving a magnetic mat disposed adjacent the diaphragm in response to application of said electromagnetic field to said mat in a direction away from lungs within the human body.

15. The method according to claim 14; further comprising
   generating a second electromagnetic field that is in a direction opposite to said electromagnetic field; and
   moving the magnetic mat in a direction toward said lungs.

16. A method for assisting diaphragm movement within a human body, the method comprising:
   generating an electromagnetic field around the body with an electromagnetic assembly;
   moving a magnetic mat disposed adjacent the diaphragm in response to application of said electromagnetic field to said mat in a direction away from lungs within the human body;
   generating a second electromagnetic field that is in a direction opposite to said electromagnetic field; and
   moving the magnetic mat in a direction toward said lungs.

* * * * *